(12) United States Patent
Agrawal et al.

(10) Patent No.: US 7,700,570 B2
(45) Date of Patent: Apr. 20, 2010

(54) OLIGONUCLEOTIDE MEDIATED SPECIFIC CYTOKINE INDUCTION AND PROPHYLAXIS AND TREATMENT OF VIRAL INFECTION IN A MAMMAL

(75) Inventors: Sudhir Agrawal, Shrewsbury, MA (US); Qiuyan Zhao, Southboro, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 1343 days.

(21) Appl. No.: 10/167,825

(22) Filed: Jun. 12, 2002

(65) Prior Publication Data

US 2002/0151518 A1      Oct. 17, 2002

Related U.S. Application Data

(63) Continuation of application No. 08/848,229, filed on Apr. 30, 1997, now Pat. No. 6,426,334.

(51) Int. Cl.
*A01N 43/04* (2006.01)
*C07H 21/02* (2006.01)
*C07H 21/04* (2006.01)

(52) U.S. Cl. .................. 514/44; 536/23.1; 536/24.2; 536/24.33

(58) Field of Classification Search ............ 536/23.1, 536/24.2, 24.33; 514/44
See application file for complete search history.

(56) References Cited

U.S. PATENT DOCUMENTS 6,207,646 B1 * 3/2001 Krieg et al. ............... 514/44
6,214,806 B1 * 4/2001 Krieg et al. ............... 514/44

FOREIGN PATENT DOCUMENTS

WO   WO95/26204 A   10/1995
WO   WO98/18810 A    5/1998

OTHER PUBLICATIONS

Verthelyi., et al., 2002, The Journal of Immunology, vol. 168, p. 1659-1663.*
Dittmer et al., 2003, Current Opinion in Microbiology, vol. 6, p. 472-477.*
Mutwiri et al., 2003, Veterinary Immunology and Immunopathology, vol. 91, p. 89-103.*
Agrawal et al., 2002, Trends in Molecular Medicine, vol. 8, No. 3, p. 114-121.*
Sin et al., 2000, Intervirology, vol. 43, p. 233-246.*
Klinman et al., Proceedings of the National Academy of Sciences of USA, "CpG Motifs Present in Bacterial DNA Rapidly Induce Lymphocytes to secrete Interleukin 6, Interleukin 12, and Interferon Gamma", 93:2879-1883, 1996.
Ballas et al., The Journal of Immunology, "Induction of NK Activity in Murine and Human Cells by CpG Motifs in Oligodeoxynucleotides and Bacterial DNA", 157:1840-1845, 1996.
Agrawal, et al., TIBTECH, "Antisense Oligonucleotides: Towards Clinical Trials", 14:376-187, 1996.
Krieg et al., Antisense & Nucleic Acid Drug Development, "Oligodeoxynucleotide Modifications Determine the Magnitude of B Cell Stimulation by CpG Motifs", 6:133-139, 1996.
Zhao et al., Antisense & Nucleic Acid Drug Development, "Pattern and Kinetics of Cytokine Production Following Administration of Phosphorothioate Oligonucleotides in Mice", 7:495-501, 1997.
Grayson et al., European Journal of Immunology "Immunostimulatory DNA: Sequence Dependent Production of Potentially Harmful or Useful Cytokines", 27:3420-3426, 1997.
International Search Report issue in connection with a counterpart Patent Cooperation Treaty Application No. PCT/US98/08751.

* cited by examiner

*Primary Examiner*—Shin-Lin Chen
(74) *Attorney, Agent, or Firm*—Preti Flaherty; Wayne A. Keown

(57) ABSTRACT

The invention provides new methods for modulating specific CMI-inducing cytokines in vivo. Such new methods result in stimulation of the cytokines IL-6, IL-12 MIP-1β and MCP without substantially inducing undesired cytokines. The methods according to the invention are based upon administration of oligonucleotides containing particular structural motifs which lead to specific cytokine induction.

1 Claim, No Drawings

OLIGONUCLEOTIDE MEDIATED SPECIFIC CYTOKINE INDUCTION AND PROPHYLAXIS AND TREATMENT OF VIRAL INFECTION IN A MAMMAL

This application is a continuation of U.S. Ser. No. 08/848,229 filed Apr. 30, 1997, now issued as U.S. Pat. No. 6,426,334.

BACKGROUND OF THE INVENTION

1. Field of the Invention

The invention relates to mediation of specific cytokine induction. More particularly, the invention relates to modulating specific cytokine expression in vivo.

2. Summary of the Related Art

Cell-mediated immunity (CMI) is an important mechanism for host defense against a broad range of infectious diseases. CMI is largely controlled through expression of specific cytokines. Le and Vilcek, Laboratory Investigation 61: 588-602 (1989) teaches that the cytokine IL-6, produced mostly by B-lymphocytes, monocytes and Th2 cells, promotes release of acute phase reactants and contributes to T cell activation. Trinchieri et al., Ann. Rev. Immunol. 13: 252-276 (1995) and Res. Immunol. 146: 419-656 (1995) disclose that the recently discovered cytokine IL-12 is critical to the initiation of CMI.

IL-12 most likely acts first upon resting natural killer (NK) cells, which express the IL-12 receptor. Gazzinelli et al., Proc. Natl. Acad. Sci. USA 90: 6115-6119 (1993) teaches that upon stimulation with IL-12, NK cells produce high levels of IFN-gamma, which is a potent stimulator of macrophage effector functions against invasive pathogens, and which further enhances IL-12 synthesis by macrophages previously triggered by an infectious agent.

At another level, IL-12 appears to act by driving the differentiation of T helper cell precursors (Thp) toward production of Th1 cells, which produce IL-2, IFN-gamma and TNF-beta, thereby driving the CMI response. Seder et al., teaches that this process begins by recognition of specific antigen by Thp, which produces IL-2 and subsequently IL-12 receptor. The Thp cell then differentiates into a Th1 cell if IL-12 is present, or into a Th2 cell in an IL-4 environment. Gazzineri et al., J. Immunol. 153: 2533-2543 (1994) teaches that the Th1 cells, once differentiated, do not require IL-12 as a co-stimulatory molecule to produce cytokines and mediate resistance against pathogens.

Miller and Krangel, Crit. Rev. Immunol. 12: 17-46 (1992) and Taub et al., J. Clin. Invest. 95: 1370-1376 (1995) teach that chemokines are one superfamily of cytokines that play important roles in recruitment and activation of lymphocytes to sites of inflammation. Gallo et al., Science 274: 1393-1395 (1996) teaches that certain chemokines, such as RANTES, MIP-1α and MIP-1β can suppress the replication of macrophage-tropic HIV strains in infected T cell cultures, and therefore may play important roles in the regulation of virus replication and are potentially useful as anti-viral therapeutics.

During bacterial infections, the natural immune response is characterized by the production of various cytokines which are involved in CMI. Uyttenhove et al., J. Exp. Med. 167: 1417-1427 (1988) teaches that IL-6 production is stimulated by bacterial infection. Murray, Diagn. Microbiol. Infect. Dis. 13: 411-421 (1990) teaches that IFN-gamma is produced in response to bacterial infection. Trinchieri, Blood 84: 4008-4027 (1994) discloses IL-12 induction resulting from bacterial infection.

The bacterial components responsible for such cytokine induction have recently been investigated. Yamamoto et al., Microbiol. Immunol. 36: 983-997 (1992) showed that bacterial DNA, but not mammalian DNA, boosts lytic activity of NK cells as well as IFN-gamma production, and proposed that this effect was caused by palindromic sequences present in bacterial DNA. More recently, Klinman et al., Proc. Natl. Acad. Sci. USA 93: 2879-2883 (1996) discloses that the ex vivo induction of IL-6, IL-12 and IFN-gamma by bacterial DNA is mediated by a structural motif of an unmethylated CpG dinucleotide preceded by two purines and followed by two pyrimidines and that this effect can be duplicated by an oligonucleotide of at least eight nucleotides containing such a structural motif. These authors noted that such effects may confound studies involving antisense, gene therapy, or plasmid DNA vaccines produced in bacteria.

Interest in developing drugs modeled from microbial products that induce CMI has been expressed. Gazzinelli, Molecular Medicine Today, June 1996, pp. 258-267, notes that such compounds would have a broad application in immunotherapy. However, Gazzinelli also teaches that uncontrolled IL-12 synthesis may cause excessive activation of the immune system, resulting in severe host tissue damage and death Gazzinelli concludes such toxicity is likely to limit the use of IL-12 therapy in humans.

There is, therefore, a need for new approaches to modulating specific CMI-inducing cytokines in vivo. Such approaches should stimulate production of the desired cytokines without substantially inducing undesired cytokines and without causing unwanted toxic side effects. Ideally, such approaches should protect against infection by a pathogenic agent or against tumor development.

BRIEF SUMMARY OF THE INVENTION

The invention provides new methods for modulating specific CMI-inducing cytokines in vivo. Such new approaches result in stimulation of the cytokines IL-6, IL-12 and IFN-gamma and chemokines (MIP-1α and MIP-1β) without substantially inducing undesired cytokines. Moreover, the methods according to the invention provide protection against infection by pathogenic agents or against tumor development.

In a first aspect, the invention provides a method for elevating levels of IL-12 in a mammal, including a human. This method according to the invention comprises measuring a baseline level of IL-12 in the mammal, administering to the mammal an oligonucleotide having a structural motif which induces IL-12 expression in vivo, and measuring the level of IL-12 in the mammal after such administration, wherein the level of IL-12 measured after such administration is higher than the level of IL-12 measured before such administration. In a second aspect, the invention provides a method for elevating expression of IL-12 mRNA in a mammal, including a human. This method according to the invention comprises measuring a baseline level of IL-12 mRNA in cells from the mammal, administering to the mammal an oligonucleotide having a structural motif which induces IL-12 expression in vivo, and measuring the level of IL-12 mRNA in cells from the mammal after such administration, wherein the level of IL-12 mRNA measured after such administration is higher than the level of IL-12 mRNA measured before such administration. In a third aspect, the invention provides a method for prophylactically protecting a mammal, including a human, from infection by a pathogen. In the method according to this aspect of the invention, an oligonucleotide having a structural motif which induces IL-12 expression in vivo is administered to a mammal which is not expressing symptoms of infection by the pathogen. The oligonucleotide is administered in an amount and for a time sufficient to prevent successful infection by the pathogen In a fourth aspect, the invention provides a method for therapeutically treating a mammal, including a human, which is infected by a pathogen. In the method according to this aspect of the invention, an oligonucleotide having a structural motif which induces IL-12 expression in vivo is administered to a mammal which is infected by the pathogen. The oligonucleotide is administered in an amount and for a time sufficient to eliminate or reduce symptoms of infection by the pathogen. In a fifth aspect, the invention provides a method for reducing tumor growth in a mammal, including a human, which has a tumor. In the method according to this aspect of the invention, an oligonucleotide having a structural motif which induces IL-12 expression in vivo is administered to a mammal which has a tumor. The oligonucleotide is administered in an amount and for a time sufficient to eliminate or reduce tumor growth in the mammal.

In the methods according to each aspect of the invention, the mammal to which the oligonucleotide may be administered includes humans. Further, in the methods according to each aspect of the invention, the oligonucleotides administered to the mammals may take the form of particular preferred embodiments. In one preferred embodiment, the oligonucleotide has the nucleotide sequence $N_{n1}\text{-}\underline{N}_{n2}\text{-}\underline{CpG}\text{-}\underline{N}_{n3}\text{-}N_{n4}$, wherein N represents any nucleoside, n1 and n4 each independently represent a number from 0 to 50, n2 represents a number from 0 to 50 and n3 represents a number from 0 to 50 such that n2+n3 equals from about 6 to about 100, wherein the underlined region represents a nucleoside phosphodiester or phosphorothioate region or a mixed backbone region having phosphodiester and phosphorothioate nucleosides, wherein CpG represents a cytosine-guanosine dinucleoside phosphorothioate or phosphodiester dinucleoside, wherein the cytosine has a cytidine base having an unmethylated 5-position, and wherein at least one of n1, n2, n3, and n4 comprises four consecutive guanosine nucleosides.

DETAILED DESCRIPTION OF THE PREFERRED EMBODIMENTS

The invention relates to in vivo mediation of specific cytokine induction. The patents and publications identified in this specification are within the knowledge of those skilled in this field and are hereby incorporated by reference in their entirety.

The invention provides new methods for modulating specific CMI-inducing cytokines and chemokines in vivo. Such new approaches result in stimulation of the cytokines IL-6, IL-12 and IFN-gamma and chemokines (MIP-1α and MIP-1β) without substantially inducing undesired cytokines. Moreover, the methods according to the invention provide protection against infection by pathogenic agents or against tumor development.

In a first aspect, the invention provides a method for elevating levels of IL-12 in a mammal, including a human. This method according to the invention comprises measuring a baseline level of IL-12 in the mammal, administering to the mammal an oligonucleotide having a structural motif which induces IL-12 expression in vivo, and measuring the level of IL-12 in the mammal after such administration, wherein the level of IL-12 measured after such administration is higher than the level of IL-12 measured before such administration. Preferably, the level of IL-12 is measured in serum and reference is made to serum IL-12 levels or serum IL-12 protein levels. In one preferred embodiment, the levels of IL-12 are measured using ELISA analysis, with antibodies specific for IL-12 protein. However, those skilled in the art will recognize that numerous methods for determining specific protein concentrations are known in the art, and that any of these methods may be used, including without limitation radioimmunoassay, quantitative immunoprecipitation, radial immunodiffusion and cell-based functional assays for IL-12 activity. Preferably, the levels of IL-12 are measured from about 1 minute to about 1 day before administration of the oligonucleotides, to minimize the likelihood of intervening infection, which could alter IL-12 baseline levels. It is preferred that the levels of IL-12 be measured again from about eight hours to about 4 days after oligonucleotide administration, and most preferably about 1 day after oligonucleotide administration. In a preferred embodiment, the method according to this aspect according to the invention also results in increased levels of IL-6 and/or IFN-gamma, either or both of which can be conveniently measured as described above for IL-12. In particularly preferred embodiments, post-administration IL-6 and/or IFN-gamma levels are measured from about one day to about one week after administration of the oligonucleotide, and most preferably about three days after administration of the oligonucleotide.

In a second aspect, the invention provides a method for elevating expression of IL-12 mRNA in a mammal, including a human. This method according to the invention comprises measuring a baseline level of IL-12 mRNA in cells from the mammal, administering to the mammal an oligonucleotide having a structural motif which induces IL-12 expression in vivo, and measuring the level of IL-12 mRNA in cells from the mammal after such administration, wherein the level of IL-12 mRNA measured after such administration is higher than the level of IL-12 mRNA measured before such administration. Preferably, the level of IL-12 mRNA is measured in lymphoid cells, and most preferably in extracts of lymphoid cells. In one preferred embodiment, the lymphoid cells are peripheral blood lymphocytes. In a preferred embodiment, the levels of IL-12 mRNA are measured using RNAse protection assay analysis, with primers and probes specific for IL-12 mRNA. However, those skilled in the art will recognize that numerous methods for determining specific mRNA concentrations are known in the art, and that any of these methods may be used, including without limitation dot blotting, slot blotting, Northern blotting, in situ hybridization, and in vitro translation coupled with cell-based functional assays for IL-12 activity. Preferably, the levels of IL-12 mRNA are measured from about 1 minute to about 1 day before administration of the oligonucleotides, to minimize the likelihood of intervening infection, which could alter IL-12 mRNA baseline levels. It is preferred that the levels of IL-12 be measured again from about four hours to about 2 days after oligonucleotide administration, and most preferably from about four hours to about 1 day after oligonucleotide administration. Preferably, the peak levels of IL-12 mRNA should exceed the baseline levels by about 10-fold or more. In a preferred embodiment, the method according to this aspect according to the invention also results in increased levels of IL-6 mRNA, which can be conveniently measured as described above for IL-12 mRNA. In particularly preferred embodiments, post-administration IL-6 mRNA levels are measured from about four hours to about 1 day after administration of the oligonucleotide. Most preferably peak levels of IL-6 mRNA should exceed baseline levels by about 8-fold or more.

In a third aspect, the invention provides a method for prophylactically protecting a mammal, including a human, from infection by a pathogen. In the method according to this aspect of the invention, an oligonucleotide having a structural motif which induces IL-12 expression in vivo is administered to a mammal which is not expressing symptoms of infection by the pathogen. The oligonucleotide is administered in an amount and for a time sufficient to prevent successful infection by the pathogen. Preferably, such administration should be parenteral, oral, sublingual, transdermal, topical, intranasal or intrarectal. Preferably, the oligonucleotide should be formulated in a physiologically acceptable carrier or diluent, including without limitation saline and/or an adjuvant. Administration of the oligonucleotides can be carried out using known procedures at dosages and for periods of time effective to prevent symptoms or surrogate markers of the disease from appearing. When administered systemically, the oligonucleotide is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more IL-12 inducing oligonucleotide to an individual as a single treatment episode. In a preferred embodiment, after the oligonucleotide is administered, one or more measurement is taken of levels of IL-12 protein or mRNA, to assess the effectiveness of the prophylaxis.

In a fourth aspect, the invention provides a method for therapeutically treating a mammal, including a human, which is infected by a pathogen. In the method according to this aspect of the invention, an oligonucleotide having a structural motif which induces IL-12 expression in vivo is administered to a mammal which is infected by the pathogen. Preferably, the oligonucleotide is administered as soon as possible after symptoms are first observed, and most preferably within one day to one week from the time at which symptoms are first observed. The oligonucleotide is administered in an amount and for a time sufficient to eliminate or reduce symptoms of infection by the pathogen. Preferably, such administration should be parenteral, oral, sublingual, transdermal, topical, intranasal or intrarectal. Preferably, the oligonucleotide should be formulated in a physiologically acceptable carrier or diluent, including without limitation saline and/or an adjuvant. Administration of the oligonucleotides can be carried out using known procedures at dosages and for periods of time effective to reduce or eliminate symptoms or surrogate markers of the disease. It may be desirable to administer simultaneously, or sequentially a therapeutically effective amount of one or more IL-12 inducing oligonucleotide to an individual as a single treatment episode. In a preferred embodiment, after the oligonucleotide is administered, one or more measurement is taken of levels of IL-12 protein or mRNA, to assess the effectiveness of the intervention.

In a fifth aspect, the invention provides a method for reducing tumor growth in a mammal, including a human, which has a tumor. In the method according to this aspect of the invention, an oligonucleotide having a structural motif which induces IL-12 expression in vivo is administered to a mammal which has a tumor. The oligonucleotide is administered in an amount and for a time sufficient to eliminate or reduce tumor growth in the mammal. Preferably, the oligonucleotide is administered as soon as possible after the tumor is first detected. The oligonucleotide is administered in an amount and for a time sufficient to eliminate or reduce symptoms of infection by the pathogen. Preferably, such administration should be parenteral, oral, sublingual, transdermal, topical, intranasal or intrarectal. Preferably, the oligonucleotide should be formulated in a physiologically acceptable carrier or diluent, including without limitation saline and/or an adjuvant. Administration of the oligonucleotides can be carried out using known procedures at dosages and for periods of time effective to reduce or eliminate symptoms or surrogate markers of the disease. When administered systemically, the oligonucleotide is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more IL-12 inducing oligonucleotide to an individual as a single treatment episode. In a preferred embodiment, after the oligonucleotide is administered, one or more measurement is taken of levels of IL-12 protein or mRNA, to assess the effectiveness of the intervention.

In the methods according to each aspect of the invention, the mammal to which the oligonucleotide may be administered includes humans. Further, in the methods according to each aspect of the invention, the oligonucleotides administered to the animals may take the form of particular preferred embodiments. In one preferred embodiment of the methods according to each aspect of the invention, the oligonucleotide has the nucleotide sequence $N_{n1}$-$\underline{N}_{n2}$-CpG-$\underline{N}_{n3}$-$N_{n4}$, wherein N represents any nucleoside, n1 and n4 each independently represent a number from 0 to 50, n2 represents a number from 0 to 50 and n3 represents a number from 0 to 50 such that n2+n3 equals from about 6 to about 100, wherein the underlined region represents a nucleoside phosphodiester or phosphorothioate region or a mixed backbone region having phosphodiester and phosphorothioate nucleosides, wherein CpG represents a cytosine-guanosine dinucleoside phosphorothioate or phosphodiester dinucleoside, wherein the cytosine has a cytidine base having an unmethylated 5-position, and wherein at least one of n1, n2, n3, and n4 comprises four consecutive guanosine nucleosides. Most preferably, n1 and n4 each independently represent a number from 0 to 10, n2 represents a number from 0 to 20 and n3 represents a number from 0 to 20 such that n2+n3 equals from about 6 to about 40.

In another preferred embodiment, the oligonucleotide has the nucleotide sequence $N_{n1}$-$\underline{N}_{n2}$-Pu-Pu-CpG-Py-Py-$\underline{N}_{n3}$-$N_{n4}$, wherein N represents any nucleoside, Pu represents a purine, Py represents a pyrimidine, n1 and n4 each independently represent a number from 0 to 50, n2 represents a number from 0 to 50 and n3 represents a number from 0 to 50 such that n2+n3 equals from about 2 to about 100, wherein the underlined region represents a nucleoside phosphodiester or phosphorothioate region or a mixed backbone region having phosphodiester and phosphorothioate nucleosides, and wherein CpG represents a cytosine-guanosine dinucleoside phosphorothioate or phosphodiester dinucleoside, wherein the cytosine has a cytidine base having an unmethylated 5-position. Most preferably, n1 and n4 each independently represent a number from 0 to 10, n2 represents a number from 0 to 20 and n3 represents a number from 0 to 20 such that n2+n3 equals from about 2 to about 40.

In another preferred embodiment, the region(s) of the oligonucleotide outside the underlined region, when present, may optionally include polymers of two or more deoxyribonucleotide, ribonucleotide, or 2'-O-substituted ribonucleotide monomers, or any combination thereof. Such polymers may be internucleosidically linked by any internucleoside linkage, including without limitation, phosphodiester, phosphotriester, phosphorothioate, phosphorodithioate, phosphoramidate, alkylphosphonate, carbamate, and amide (PNA) linkages, or any combination of the same. Those skilled in the art will recognize that the type of internucleoside linkages in such region(s) is not critical. For purposes of the invention the term "2'-O-substituted" means substitution of the 2' position of the pentose moiety with an —O-lower alkyl group containing 1-6 saturated or unsaturated carbon atoms, or with an O-aryl or allyl group having 2-6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group, but not with a 2'-H group. Such region(s) also encompass such polymers having chemically modified bases or sugars and/or having additional substituents, including without limitation lipophilic groups, intercalating agents, diamines and adamantane.

The methods according to the invention are useful for preventing or treating pathogenic infections in animals, such as in mice. In addition, the methods according to the invention are useful as prophylactic and therapeutic approaches to pathogenic infections in humans. Such pathogens include numerous pathogenic viruses. Preferred viruses include without limitation human immunodeficiency virus (type 1 or 2), influenza virus, herpes simplex virus (type 1 or 2), Epstein-Barr virus, human and murine cytomegalovirus, respiratory syncytial virus, hepatitis B virus, hepatitis C virus and papilloma virus. Preferred pathogens also include eukaryotic or prokaryotic pathogens, including without limitation, *Plasmodium falciparum, Plasmodium malarie, Plasmodium ovale, Schistosoma* spp., *Streptococcus* spp., *Staphylococcus* spp., *Pneumococcus* spp., *Neisseria* spp., *Vibrio* spp., *E. coli* and *Mycobacterium tuberculosis*.

The following examples are intended to further illustrate certain aspects of preferred embodiments of the invention and are not intended to be limiting in nature.

Example 1

Preparation of Phosphorothioate Oligodeoxynucleotides

Phosphorothioate oligodeoxynucleotides (PS-oligonucleotides) were synthesized on an automated synthesizer (Model 8700, Millipore, Bedford, Mass.) using conventional phosphoramidite chemistry. The oligonucleotide was deprotected by treatment with concentrated ammonium hydroxide for 12 hours at 55° C., then was purified by reverse phase HPLC and lyophilized to dryness prior to use.

Example 2

Treatment of Mice for Cytokine Measurements

CD1 mice (19-21 g, male) were purchased from Charles River Laboratory (Wilmington, Mass.) and maintained in a pathogen-free facility at the University of Massachusetts Medical Center (Worcester, Mass.). For each experimental group, 50 mg/kg PS-oligonucleotide in 250 microliters sterile PBS was administered intraperitoneally (i.p.) to the mice. In these experiments, the oligonucleotide was complementary to the rev gene of HIV-1 and had the nucleotide sequence 5'-TCGTCGCTGTCTCCGCTTCTTCTTGCC-3' [SEQ. ID NO. 1]. This sequence, which has previously been reported to be immunogenic (Branda et al., Biochem. Pharmacol. 45: 2037-2043 (1993)) contains multiple CpG dinucleotides, none of which possess the purine-purine-CpG-pyrimidine-pyrimidine structural motif. One group of control mice was similarly injected with equal volumes of sterile PBS. Each day for the following seven days after injection, four mice in each group were sacrificed, and peripheral blood and spleens were harvested for further studies.

Example 3

Multi-Probe Rnase Protection Assay for Cytokine mRNA Expression

Mice were treated as described in Example 2. The levels of spleen cytokine mRNA expression were quantified by multi-probe RNase protection assay using murine cytokine kits (mck-Pharmigen, San Diego, Calif.) Briefly, RNA was extracted from mouse spleens by homogenization in Tri-zol (Life Technologies, Gaithersburg, Md.), and hybridized with the appropriate probe sets (mck-1, mck-2) at 56° C. overnight. The reaction mixtures were digested with Rnase to remove free probe and other single stranded RNA. Undigested probe: RNA duplexes were extracted, purified and analyzed on denaturing polyacrylamide gels followed by autoradiography.

Example 4

ELISA Assays for Cytokines in Serum

Mice were treated as described in Example 2. Serum levels of IL-2, IL-4, IL-6, IL-12, IFN-gamma and MCP-1 were measured using commercial ELISA kits BioSource International (Camarillo, Calif.). All other serum cytokines were measured by sandwich ELISA using monoclonal antibodies (mAbs) and standards purchased from PharMingen (San Diego, Calif.) with the exception of MIP-1β, which was obtained from R&D Systems (Minneapolis, Minn.) ELISA was carried out according to the manufacturer's instructions. Briefly, ELISA plates (Costar, Cambridge, Mass.) were coated with appropriate unconjugated capture mAbs at 5 micrograms/ml in PBSN buffer (PBS with 0.05% sodium azide, pH 9.6) and incubated overnight at 4° C. After a blocking step (10% FCS/PBS, 2 hr., 25° C.), standards and serial dilutions of serum samples were added in duplicate in 10% FCS/PBS and incubated overnight at 4° C. After extensive washing, appropriate biotin-conjugated detecting antibodies were added to the wells at 1 microgram/ml in 10% FCS/PBS and incubated at 25° C. for 2 hours. Wells were then washed and incubated with streptavidin-peroxidase (Sigma, St Louis, Mo.) at 25° C. for 1 hour. Plates were washed thoroughly and enzyme substrate ABTS (2,2-azino-di-(3-ethyl-benz-thiazoline sulfonate 6)) and $H_2O_2$ (Kirkegaard and Perry, Gaithersburg, Md.) were added. The reaction was developed at room temperature and colorimetric changes were detected using a Ceres 900 HDI (Bio-Tek Instruments, Winooski, Vt.). Cytokine levels (pg/ml) in serum were calculated against respective standard curves for each cytokine. Measures of IL-12 were performed identically, but in a separate set of experiments. Mean values and standard deviations for each group of four mice were calculated.

Example 5

Oligonucleotide-mediated Protection Against Lethal Murine Cytomegalovirus (mCMV) Infection PS-oligonucleotides HYB-0272 and HYB-0352 were synthesized as described in Example 1. HYB-0272 has the following nucleotide sequence: 5'-TCCATGACGTTCCTGAT-GCTTTTTGGGGG-3' [SEQ. ID NO. 2]. HYB-0352 has the following nucleotide sequence: 5'-TCCATGAGCTTCCT-GATGCTTTTTGGGGG-3' [SEQ. ID NO. 3]. The only difference between HYB-0272 and HYB-0352 is that the CpG in the former is replaced by a GpC in the latter.

Weanling 8-11 g specific pathogen-free female BALB/c mice were obtained from Simonsen Laboratories (Gilroy, Calif.). The animals were quarantined 24 hours prior to use, fed Wayne Lab Blox and tap water ad libitum and maintained in an AAALAC-accredited laboratory animal research center. Strain Smith of mCMV (American Type Culture Collection, Rockville, Md.) was passaged in mice, with salivary glands being taken and pooled as a 10% homogenate. The pool was frozen at −80° C. and titrated in mice prior to use. Lyophilized oligonucleotides were prepared in sterile physiological saline on the first day of the experiment and maintained at 4° C. for the duration of the experiment. For positive control experiments, gangcyclovir was similarly prepared in sterile physiological saline.

Groups of 15 mice (with 25 placebo controls) were infected i.p. with a 1:7 dilution of virus. Administration of oligonucleotide was initiated i.p. 24 hours prior to virus inoculation and repeated at the same dose once daily for four more days. Oligonucleotide dosages were 25, 10 and 5 mg/kg/day. For positive controls, Gangcyclovir was administered beginning 24 hours after virus inoculation and repeated at the same dose once daily for 8 days. Ten of the mice (and 20 placebo controls) were observed for death daily for 21 days. Differences in survivor numbers were analyzed using chi square analysis with Yates' correction. Increases in mean day to death were evaluated using the t-test.

The remaining 5 infected and treated mice in each group were killed on day 5 and their spleens and salivary glands were removed and assayed for virus titer. Spleens were each weighed upon removal from the animals. For viral titer assay, each organ removed from an animal was homogenized to 10% (w/v) suspension in minimum essential medium containing 2% fetal bovine serum, bicarbonate buffer and gentamycin. Each was diluted through a series of $log_{10}$ dilutions which were assayed in triplicate in mouse embryo fibroblast (3T3) cells. Virus cytopathic effect (CPE) was determined microscopically after a 6 day incubation at 37° C. Calculation of titer, expressed in $log_{10}$ cell culture infectious doses/g tissue, was done by the well known 50% endpoint dilution method. Decreases in mean virus titers and increases in spleen weights were evaluated using the t-test.

Treatment with HYB-0272 had a significant inhibitory effect on mCMV infection as shown by a significant number of survivors among infected mice treated with the lowest dose, increase in mean day to death in the mid- and low-dosage groups, and reduction in spleen and salivary titers. This compound actually hastened death in infected animals in the high dosage group. HYB-0352 was only marginally active, with a maximum increase in survivors of 25% (P.0.05). Spleen virus titers were essentially not reduced by treatment with this compound. All controls were as expected.

Example 6

Inhibition of Tumor Growth

LS-174T human colon carcinoma cells ($1\times10^6$ cells) were inoculated subcutaneously (s.c.) into the left flank of athymic mice. A single dose of HYB-0272 (1 or 10 mg/kg/day) or HYB-0352 (10 mg/kg/day) was injected s.c. into the right flank of mice when tumor size reached 80 to 100 mg, about 1 week after cell inoculation. Tumor volumes were obtained from daily measurement of the longest and shortest diameters and calculation by the formula, $4/3\pi r^3$ where r=(length+width)/4. At each indicated time, two animals from the control and oligonucleotide-treated groups were killed, and tumors were removed and weighed. The results showed that the size of the tumor in the animal treated with 10 mg/kg/day HYB-0272 was smaller from two days after injection onward than the tumor treated with 10 mg/kg/day HYB-0352.

What is claimed is:

1. A method for therapeutically treating a mammal which is infected by a virus, the method comprising administering to the infected animal an oligonucleotide having a structural motif which induces IL-12 expression in vivo in an amount and for a time sufficient to eliminate or reduce symptoms of infection by the virus, wherein the oligonucleotide has the nucleotide sequence $N_{n1}$-Nn2-CpG-Nn3-$N_{n4}$, wherein N represents any nucleoside, n1 and n4 each independently represent a number from 0 to 50, n2 represents a number from 0 to 50 and n3 represents a number from 0 to 50 such that n2+n3 equals from about 6 to about 100, wherein the underlined region represents a nucleoside phosphodiester or phosphorothioate region or a mixed backbone region having phosphodiester and phosphorothioate nucleosides, wherein CpG represents a cytosine-guanosine dinucleoside phosphorothioate or phosphodiester dinucleoside, wherein the cytosine has a cytidine base having an unmethylated 5-position, and wherein at least one of n1, n2, n3 and n4 comprises four contiguous guanosine nucleosides.

\* \* \* \* \*